United States Patent [19]

Vora et al.

[11] 4,056,615
[45] Nov. 1, 1977

[54] LUCKNOMYCIN AND PROCESS FOR PRODUCING SAME

[75] Inventors: Vinay Chhotalal Vora, Lucknow; Amrut Vithaldas Mody, Bombay, both of India

[73] Assignee: U C B Societe Anonyme, Brussels, Belgium

[21] Appl. No.: 689,145

[22] Filed: May 24, 1976

[30] Foreign Application Priority Data

May 28, 1975 United Kingdom .............. 23342/75

[51] Int. Cl.$^2$ .............................................. A61K 35/00
[52] U.S. Cl. ................................................... 424/120
[58] Field of Search ......................................... 424/120

[56] References Cited

U.S. PATENT DOCUMENTS 3,898,327   8/1975   Nimeck et al. ...................... 424/120

*Primary Examiner*—Albert T. Meyers
*Assistant Examiner*—Daren M. Stephens
*Attorney, Agent, or Firm*—Wenderoth, Lind & Ponack

[57] ABSTRACT

Antifungal and antiprotozoal antibiotic lucknomycin is producible by culturing *Streptomyces diastatochromogenes* var. Krains in an aqueous nutrient medium under submerged aerobic conditions. Lucknomycin is active against *Candida albicans, Candida tropicalis, Candida krusei, Aspergillus niger* and more particularly against *Trichomonas vaginalis.*

7 Claims, No Drawings

LUCKNOMYCIN AND PROCESS FOR PRODUCING SAME

The present invention relates to a new antifungal and antiprotozoal agent, hereinafter referred to as "lucknomycin", and to a process for the preparation thereof.

Various antifungal antibiotics are already known but research is continuing throughout the world to discover new antifungal agents having various advantages over those already known.

We have now discovered a new antifungal agent, which we have called lucknomycin, which has been found to be effective against the growth of, in particular, *Candida albicans, Candida krusei, Candida tropicalis* and *Aspergillus niger*. It is also effective against *Trichomonas vaginalis*.

Lucknomycin has the following chemical and physical characteristics.

1. PHYSICAL CHARACTERISTICS:

1.1 Aspect: orange yellow powder 1.2 Elemental analysis: $C_{61}H_{96}N_2O_{24}$ (molecular weight 1240): Calcd. : C, 59.03%; H 7.74%; N 2.26%. Found : C, 58.92%; H, 7.58%; N, 2.29%.

1.3 Melting point:
the product starts to decompose at about 150° C. but, even at 300° C., it does not melt.

1.4 Solubility:
soluble in pyridine, dimethylformamide and dimethylacetamide; less soluble in 60% methanol, concentrated ethanol and isopropanol;

insoluble in benzene, acetone, water, chloroform, absolute ethanol, cyclohexane, ethyl acetate and diethyl ether.

In sulfuric acid, the new antifungal agent gives an intense blue coloration.

1.5 Infrared absorption spectrum:
taken from the spectrum in a KBr pellet (in cm$^{-1}$)

| | | |
|---|---|---|
| 3400 (S)* | 1465 (W) | 1075 (S) |
| 3100 (W)*** | 1390 (W) | 1045 (W) |
| 2930 (S) | 1350 (W) | 1010 (S) |
| 2860 (M)** | 1325 (W) | 995 (W) |
| 1715 (M) | 1295 (W) | 940 (W) |
| 1650 (M) | 1250 (W) | 890 (W) |
| 1600 (S) | 1185 (S) | 850 (M) |
| 1575 (W) | 1140 (W) | 835 (W) |
| 1545 (W) | 1110 (M) | 800 (W) |

Band intensities are indicated as "S", "M" and "W" respectively
*S = strong absorption
**M = medium absorption
***W = weak absorption 1.6 Ultraviolet absorption spectrum:
taken at a concentration of 1 mg./100 ml. of dimethylformamide 344 mμ ($\epsilon = 3.5 \times 10^4$)

364 mμ ($\epsilon = 5.52 \times 10^4$)

384 mμ ($\epsilon = 8.04 \times 10^4$)

408 mμ ($\epsilon = 6.6 \times 10^4$)

1.7 Optical rotation:
$[\alpha]_D^{25° C.} = 187°$ to $194°$ (c. = 0.3% in dimethylformamide at 25° C).

2. CHEMICAL CHARACTERISTICS

Lucknomycin can be classified as an aromatic heptaene antibiotic because, by the retroaldolization reaction, it gives p-N-methylaminoacetophenone.

Methanolysis, attributes to Lucknomycin a substituent of the amino sugar type, identified with an authentic sample of mycosamine.

Lucknomycin does not contain a titratable carboxyl group.

3. BIOLOGICAL CHARACTERISTICS 3.1 Antifungal spectrum.

Lucknomycin is introduced at different dilutions into a peptonedextrose medium inoculated with the organism which is to be tested. After incubation for from 2 to 5 days at 28° C., the number of microgrammes of antibiotic per milliliter of medium is determined which must be used to obtain complete inhibition of growth (MIC) of the organism in question. In order to better point out the antifungal activity of Lucknomycin, it is compared with that of other known antifungal antibiotics.

| Microorganism | Product | MIC (mcg./ml.) |
|---|---|---|
| *Candida albicans* 11651 | Lucknomycin | 0.1–0.2 |
| | Nystatin | 2.5 |
| | Amphotericin | 1.25 |
| | Pimaricin | 5 |
| *Aspergillus niger* | Lucknomycin | 0.5 |
| | Nystatin | 5 |
| | Amphotericin | 0.6 |
| | Pimaricin | 2.5 |
| *Trichophyton mentagrophytes* | Lucknomycin | 25 |
| | Nystatin | 25 |
| *Trichophyton acuminatum* | Lucknomycin | 12.5 |
| | Nystatin | 25 |
| *Trichomoras vaginalis* | Lucknomycin | <0.05 |
| | Nystatin | >10 |
| | Amphotericin B | >10 |
| | Pimaricin | >10 |
| | Metronidazole | 0.5 |
| *Candida krusei* | Lucknomycin | 0.2–0.4 |
| *Candida tropicalis* | Lucknomycin | 0.1–0.2 |

3.2 Antibacterial spectrum.

The experimental conditions are the same as for the determination of the fungal spectrum, except that the incubation time is one day at 37° C.

Lucknomycin does not exert an inhibiting activity, at a concentration of 10 mcg/ml, on the following bacteria:

*Escherichia coli*
*Klebsiella pneumoniae*
*Lactobacillus acidophilus*
*Proteus mirabilis*
*Pseudomonas aeruginosa*
*Staphylococcus aureus*
*Streptococcus faecalis*

3.3 Antiprotozoal activity.

A concentration of 0.5 mcg./ml. of the antibiotic kills 50% of individuals of a culture in full growth of *Trichomonas vaginalis* within a period of about 30 minutes.

3.4 Toxicity.

Lethal dose $LD_{50}$ in mice in mg./kg. body weight:

| Mode of administration | $LD_{50}$ |
|---|---|
| intravenous | 10–20 |
| intraperitoneal | 5–10 |
| subcutaneous | >800 |
| oral | >800 |

4. PHARMACOLOGICAL TESTS IN VIVO.

4.1 Anti-Trichomonas vaginalis activity.

This test is made in mice on a subcutaneous *Trichomonas vaginalis* abscess. Subcutaneous injections at the level of the abscess of a suspension (or solution) of the following products at various concentrations are used to determine the $ED_{50}$.

| Product | $ED_{50}$ on *Trichomonas vaginalis* (in mcg./ml.) |
|---|---|
| Lucknomycin | 12 |
| Candicidin | 24 |
| Trichomycin | 43 |
| Metronidazole | 250 |
| Pimaricin | 720 |

4.2 Anti-Candida albicans activity in gynecology.

The test is made in female rats on experimental *Candida albicans* vaginitis. Lucknomycin is compared with two reference products: Mycostatin (active principle = nystatin) and Canestene (active principle = clotrimazole).

| | | Number of cured rats/infested rats | | |
|---|---|---|---|---|
| Active principle (in mg./tablet) | | after 4 adm.* | after 8 adm.* | after 12 adm.* |
| a) lucknomycin | 5 mg. | 14/16 | 13/13 | 12/12 |
| b) clotrimazole | 20 mg. | 17/18 | 16/16 | 17/17 |
| c) nystatin | 4 mg. | 5/11 | 8/11 | 9/11 |

*adm. = administrations.
a) galenic formula of the test tablet.

| | |
|---|---|
| lucknomycin | 5 mg. |
| sodium borate | 50 mg. |
| Aerosil R 972* | 0.8 mg. |
| Precirol** | 1 mg. |
| LSNa*** | 0.8 mg. |
| Avicel pH 102**** | 52 mg. |
| Lactose FK q.s.p. | 200 mg. |

\* colloidal silica
\*\* glycerol palmitate + stearate
\*\*\* sodium lauryl-sulfate
\*\*\*\* microcrystalline cellulose b) 1/5 of a commercial tablet containing 100 mg. clotrimazole
c) 1/5 of a commercial tablet containing 20 mg. (100.000 units) nystatin.

5. THERAPEUTIC USES.

Lucknomycin is an antifungal and antiprotozoal antibiotic which has the following uses:

treatment of candidiases which may be general or superficial on the skin (dermatology) or on the buccal, vaginal or intestinal mucous membranes;

treatment of infections of cavities due to *Trichomonas vaginalis* (trichomoniases) and more particularly the therapeutic use in gynecology;

veterinary use for the treatment of mycotic infections and curative activity against prostatic hypertrophy.

It can also be used in agriculture to combat vegetal mycoses.

Lucknomycin may be administered orally, topically or intravaginally. The physician will indicate daily dosage. Thus for example in the treatment of vaginitis, lucknomycin may be administered intravaginally in a dosage of two vaginal tablets per day containing each 10 to 50 mg. lucknomycin per tablet of 800 to 900 mg. during two to three weeks.

5.1 Examples of formulation of tablets for use in gynecology.

| | | |
|---|---|---|
| Lucknomycin | 10 | mg. |
| sodium bicarbonate | 2.65 | mg. |
| tartaric acid | 3.65 | mg. |
| Aerosil R 972 | 0.8 | mg. |
| Precirol | 1 | mg. |
| LSNa | 0.8 | mg. |
| Avicel pH 102 | 52 | mg. |
| Lactose FK q.s.p. | 200 | mg. |
| or else | | |
| Lucknomycin | 10 | mg. |
| urea | 25 | mg. |
| Lactose SD } | 70 | mg |
| Avicel } | | |
| magnesium stearate } | | |

5.2 Examples of antifungal formulations for dermatological use.

Besides the usual carriers, appropriate amounts of an anti-inflammatory agent, a large spectrum antibiotic (or antiseptic) and/or an antihistamine may be added to the following formulations:

| Ointment | | |
|---|---|---|
| Lucknomycin | 500 | mg. |
| dimethylacetamide | 10 | ml. |
| vaseline 70% } q.s.p. | 100 | g. |
| liquid paraffin } | | |

| Cream | | |
|---|---|---|
| Lucknomycin | 500 | mg. |
| dimethylacetamide | 10 | g. |
| mixture of glycerol mono- and distearate | 12.68 | g. |
| Crodawax A22 | 0.55 | g. |
| Nipagin M* | 0.114 | g. |
| Nipasol** | 0.045 | g. |
| Tween 40*** | 0.5 | g. |
| aqua dist. q.s.p. | 100 | g. |

| Anhydrous base | | |
|---|---|---|
| Lucknomycin | 500 | mg. |
| dimethylacetamide | 10 | g. |
| Tween 40 | 0.5 | g. |
| bees wax | 3.5 | g. |
| stearyl alcohol | 20 | g. |
| glycerol q.s.p. | 100 | g. |

| Gel | | |
|---|---|---|
| Lucknomycin | 1000 | mg. |
| dimethylacetamide | 98 | g. |
| glycerol | 98 | g. |
| nordihydroguaieretic acid | 0.2 | g. |
| citric acid | 0.1 | g. |
| Carbopol 940**** | 2 | g. |
| Tween 40 | 1 | g. |
| triethaolamine q.s. | | |

\*methyl hydroxybenzoate
\*\*propyl hydroxybenzoate
\*\*\*polyoxyethylenesorbitan monopalmitate (ATLAS)
\*\*\*\*acrylic acid polymer (GOODRICH)

6. DESCRIPTION of the MICROORGANISM.

The strain used for the production of lucknomycin has been subjected to an identification study by the Centraalbureau voor Schimmelcultures of Baarn (Holland) and has been deposited there under strain number CBS 101.74. The study showed that this microorganism clearly belongs to the species *Streptomyces diastatochromogenes* (Krains) Waksman and Henrici in its most essential characteristics. The only difference, the non-utilization of sucrose, is not of such importance as to constitute proof of a new species. *S. bottropensis* Waksman 1956, *S. phaeophaciens* Maeda et al., 1952 and also *S. luteogriseus* Schmitz et al., 1964, are also very close and may possibly be considered as synonyms as previously indicated by Hutter in 1967 for *S. bottropensis* and *S. phaeophaciens*.

For the purpose of studying its morphology and culture characteristics, the organism was cultivated (specimen spores in distilled water taken with a platinum loop from cultures in slant test tubes) in the media mentioned below for from 10 to 14 days at 28° ± 1° C. The well sporulated cultures in Petri dishes were observed directly with an optical microscope. The specimens for study under an electron microscope were obtained by carefully pressing copper grids coated with "farmvar" on the sporulated mycelium. Observations were also recorded with regard to the characteristics of the culture, particularly the colors of the aerial mycelium and of the mycelium in the substrate (Maers and Paul 1950) and with regard to any changes of coloration of the media.

6.1 Color:

| | Media | Color of aerial mycelium | color of mycelium in the substrate | soluble pigment |
|---|---|---|---|---|
| 1. | Oatmeal-agar | brownish-grey | pale brown | none |
| 2. | Mineral salt-starch-agar | grey | pale yellow | none |
| 3. | Asparagine-dextrose-agar | grey | pale yellow | none |
| 4. | Yeast-malt-agar | grey | pale brown | none |
| 5. | Czapek agar | light grey | light grey | none |
| 6. | Conn agar | white to sandy | pale brown | none |
| 7. | Nutrient agar | bronze-brown | fawn | brown |
| 8. | Tomato-oatmeal-agar | brownish-grey | pale brown | none |
| 9. | Hickey-Tresner agar | olive green | amber yellow | none |
| 10. | Potato-agar | white to slate grey | maple sugar | light brown |
| 11. | Molasses-agar | grey | dark brown | none |

6.2 Microscopic characteristics.

Morphology of the spore chains:

Division spirals. The spirals are open with 4 to 6 turns. On maturity, the chains of spores have from 10 to 50 spores per chain. The sporophore branches have a sympodial arrangement. The spores are elliptical. The spore surface is smooth.

Color of colony: color of the aerial mass in various shades of greys on yeast-malt-agar, oatmeal-agar, glycerol-asparagine-agar and salt-starch-agar.

Reverse side of colony: no distinctive pigments (olive brown on yeast-malt-agar, yellowish-brown to brown with yellow edge on oatmeal-agar and greyish-yellow with some dark brown spots on glycerol-asparagine-agar and salt-starch-agar).

Color in medium: formation of melanoid pigments in peptone-yeast-iron-agar and tyrosine-agar. No pigment in yeast-malt-agar, oatmeal-agar, salt-starch-agar and glycerol-asparagine-agar.

| 6.3 Biochemical characteristics. | |
|---|---|
| Production of melamine | positive |
| decomposition of tyrosine | positive |
| production of hydrogen sulfide | positive |
| proteolysis (gelatine) | positive |
| reduction of nitrates | negative |
| utilization of carbon | | arabinose, rhamnose, glucose, galactose, fructose, mannose, lactose, maltose, dextrose, glycerol, and salicine are completely utilized;
xylose, raffinose, starch, inositol, mannitol and sodium acetate are partially utilized;
sucrose, inulin, sorbitol and sodium citrate are not utilized.

Lucknomycin is obtained when the elaborating microorganism is grown in an aqueous nutrient medium under submerged aerobic conditions. For the preparation of limited amounts of the substance, surface cultures and bottles can be used. The organism is grown in a nutrient medium containing a carbon source, for example an assimilable carbohydrate, and a nitrogen source, for example an assimilable nitrogen compound or protein material. Preferred carbon sources include arabinose, rhamnose, glucose, galactose, fructose, mannose, lactose, maltose, dextrose, glycerol, salicine, xylose, raffinose, starch, inositol, mannitol and sodium acetate. Preferred nitrogen sources include ammonium sulfate, corn steep liquor, peptone, malt extract and cottonseed protein. Use may advantageously also be made of combinations of these carbon and nitrogen sources. If desired, traces of metals, for example, zinc, magnesium, manganese, cobalt, iron and the like, can but need not be added to the fermentation medium, since for the preparation of the culture medium, use is made of tap water and unpurified raw materials.

Lucknomycin is produced in the temperature range permitting satisfactory growth of the microorganism, namely, between 20° and 32° C. and preferably between 27° and 29° C. The optimum fermentation time may vary from 2 to 10 days. The culture medium should preferably have an initial pH value close to 7.0. The final pH depends upon the presence of buffers and is also preferably about 7.0 at the time sterilization is effected.

When fermentation is carried out in vessels of large dimensions, it is preferable to use the vegetative form, rather than the spore form, of the microorganism for inoculation to avoid any lag in the production of lucknomycin and to make better use of the fermentation equipment. For this reason, it is desirable to produce a vegetative inoculum in a nutrient culture broth by inoculating this broth with an aliquot from a soil or a slant culture. When a young and active vegetative inoculum has thus been obtained, it is transferred aseptically to larger vessels. The medium used for producing a vegetative inoculum may be identical to or different from the medium used for the large scale production of lucknomycin, provided that good growth of the microorganism is ensured.

The analytical data obtained with lucknomycin attribute to this compound the formula $C_{61}H_{96}N_2O_{24}$. Lucknomycin is soluble in pyridine, dimethylformamide, dimethylacetamide; it is less soluble in 60% methanol, ethanol and isopropanol and it is insoluble in benzene, acetone, water, chloroform, absolute ethanol, cyclohexane, ethyl acetate and ether.

Different processes may be used for isolating and purifying lucknomycin, for example solvent extraction, gel chromatography and liquid-liquid distribution in a Craig apparatus. Solvent extraction processes are preferred for industrial recovery because they are quicker and less expensive.

Preferred purification processes include those using "Merckogel" 500 or "Sephadex" LH 20.

In the preferred recovery process, lucknomycin is recovered from its culture medium by separation of the mycelium and undissolved solids by conventional means, such as by filtration or by centrifugation. The antibiotic is then removed from the filtered or centrifuged broth by extraction with normal butanol. After draining and filtration (or centrifugation), the mycelium is extracted with an alcohol (ethanol or methanol). This extract is concentrated and the insoluble matter is treated successively with hexane (or petroleum ether), chloroform and diethyl ether in order to eliminate traces of an antibacterial polypeptide substance which is of no interest. The insoluble material is then washed with acetone and dried in vacuo. Additional purification or a purification of the residues containing lucknomycin may be effected by gel chromatography, using, for example, dimethylformamide as eluent. The eluate from the chromatographic column is concentrated in vacuo at a temperature of at most 40° C. and the lucknomycin is precipitated with diethyl ether or a 1:1 mixture of diethyl ether and hexane and recovered by filtration or centrifugation.

The new compound of the invention can be used against the following microorganisms: *Aspergillus niger, Candida albicans, Candida krusei, Candida tropicalis, Saccharomyces cerevisiae* and *Trichomonas vaginalis.* It is moderately active against *Trichophyton mentagrophytes* and *Trichophyton acuminatum.* It is inactive against the following bacteria: *Escherichia coli, Klebsiella pneumoniae, Lactobacillus acidophilus, Proteus mirabilis, Pseudomonas aeruginosa, Staphylococcus aureus* and *Streptcoccus faecalis.*

7. EXAMPLES.

The following Examples are given for the purpose of illustrating the present invention.

EXAMPLE 1

Fermentation of Streptomyces diastatochromogenes for the production of lucknomycin.

Germination stage

A lyophilized culture of *S. diastatochromogenes* var. Krains is added to a 500 ml. flask, capable of being shaken, containing 100 ml. of the following sterile medium:

| | |
|---|---|
| bacto-beef extract* | 3 g. |
| bacto-peptone | 5 g. |
| dextrose | 10 g. |
| yeast extract* | 5 g. |
| tap water | 1000 ml. |

(*Difco Laboratories, Detroit, Michigan, U.S.A.) in which the pH is adjusted to 7.2 with an aqueous solution of sodium hydroxide.

The flask and its contents are incubated for 2 days at 28° ± 1° C. on a rotary shaker (250 r.p.m., stroke 2 inches (50.8 mm.)).

Inoculum Preparation Stage

A charge of inoculum of about 6 liters is prepared by the following method:

10 ml. of inoculum (from the germination stage) are transferred to each of a series of flasks, each containing 200 ml. of the following sterile medium:

| | |
|---|---|
| glycerol | 10 ml. |
| L-asparagine** | 1 g. |
| dipotassium hydrogen phosphate*** | 1 g. |
| yeast extract* | 0.5 g. |
| tap water | 1000 ml. |

*Difco Laboratories, Detroit, Michigan, U.S.A.
**BDH Chemicals Ltd., Poole, Great Britain.
***J. T. Baker Chemicals Co., New Jersey, U.S.A.

The flasks and their contents are incubated for 2 days at 28° ± 1° C. on a rotary shaker (250 r.p.m., stroke 2 inches (50.8 mm.)). The broths are combined and transferred aseptically to a sterile inoculum flask.

6 liters of inoculum are transferred aseptically to a 100-liters fermenter containing 60 liters of the following sterile medium:

| | |
|---|---|
| groundnut flour | 900 g. |
| dextrose (cerelose) | 900 g. |
| sodium chloride | 30 g. |
| calcium carbonate | 6 g. |
| yeast extract | 6 g. |
| groundnut oil | 60 ml. |
| "Rhodosil 410" anti-foaming agent (Rhone-Poulenc, Paris, France) or some other appropriate anti-foaming agent | 3 ml. |
| tap water to make | 60 liters |

The pH is adjusted to between 6.9 and 7.0 before sterilization and aerobic fermentation is carried out for 48 hours (until the volume of the cells represents about 10 to 15% of the total volume) under the following conditions:

| | |
|---|---|
| temperature | 28 ± 1° C. |
| admission of sterile air | 60 liters/minute |
| pressure | 0.49 kg./cm.$^2$ gauge |
| agitation | 300 r.p.m. |

Fermentation Stage

A charge of 30 liters of inoculum is transferred aseptically to a 400-liter fermenter containing the following medium:

| | |
|---|---|
| flour | 6000 g. |
| glucose syrup (containing 60% of cerelose) | 9000 g. |
| sodium chloride | 1500 g. |
| calcium carbonate | 300 g. |
| yeast extract | 300 g. |
| groundnut oil | 3 liters |
| anti-foaming agent (Rhodosil 410) | 15 liters |
| tap water | 300 liters |

Fermentation is carried out at 28 ± 1° C., while stirring at 200 r.p.m., with the admission of air at a pressure of 0.49 kg/cm.$^2$ gauge and at the rate of 300 liters per minute. During the fermentation period of 5 days, samples were taken at different times from the fermentation broth and titrated for the production of antibiotic by the spectrophotometric method. The washed mycelium is extracted with ethanol and the optical density of the ethanol extract is measured at 383 mμ with a spectrophotometer. The calibrated curve of pure lucknomycin is plotted and the content of the samples is calculated by reference to this curve.

EXAMPLE 2

Production of Lucknomycin in Various Media.

Using the procedure described in Example 1, a lyophilized culture of *S. diastatochromogenes* var. Krains is subjected to germination. After shaking for 2 days at 28 ± 1° C., the cellular material is collected by centrifuging the fermentation mixture in a sterile flask. The solid material is washed by centrifuging twice with 100 ml. amounts of sterile distilled washing water and is then suspended in 100 ml. of sterile distilled water. The suspension is used as a 10% inoculum in various synthetic media for the fermentation and determination of the production of lucknomycin. The fermentation tests are carried out in flasks which are shaken and the spectrophotometric method of determination of lucknomycin described in Example 1 is used. The results of these tests are shown in the following Table:

| Medium (% by weight) | Shaking time (days) | Lucknomycin in micrograms/ml |
|---|---|---|
| groundnut flour: 2% glycerol: 1% sodium chloride: 0.5% calcium carbonate: 0.1% | 4 | 30 |
| groundnut flour: 2% glycerol: 1% sodium chloride: 0.5% calcium carbonate: 0.1% groundnut oil: 1% | 4 | 91 |
| soya flour: 2% glycerol: 1% sodium chloride: 0.5% calcium carbonate: 0.1% groundnut oil: 1% | 4 | 71 |
| groundnut flour: 2% cerelose: 1.5% sodium chloride: 0.5% calcium carbonate: 0.1% groundnut oil: 1% | 4 | 160 |
| groundnut flour: 2% glucose syrup: 3% sodium chloride: 0.5% calcium carbonate: 0.1% groundnut oil: 1% | 4 | 212 |

EXAMPLE 3

Effect of Ammonium Sulfate and Organic Nitrogen on the Yield of Lucknomycin.

Experiments are carried out in 500 ml. conical flasks containing 100 ml. of the following medium, supplemented by organic nitrogen sources of various kinds or with ammonium sulfate at optimum levels:

| | |
|---|---|
| groundnut flour | 2% by weight/volume |
| cerelose | 1.5% by weight/volume |
| sodium chloride | 0.5% by weight/volume |
| calcium carbonate | 0.1% by weight/volume |

A 10% inoculum as described in Example 2 is added and the flasks are shaken on a rotary shaker (250 r.p.m., stroke 2 inches (50.8 mm) at 28 ± 1° C. for 72 hours, the following titres of lucknomycin being obtained:

| percentage of nitrogen (weight/volume) | micrograms/ml. of lucknomycin |
|---|---|
| 0.1% ammonium sulfate | 24 |
| 0.1% corn steep liquor | 45 |
| 0.1% peptone | 70 |
| 0.1% malt extract | 100 |
| 0.5% cotton seed protein | 100 |
| control | 91 |

EXAMPLE 4

Extraction and Purification of Lucknomycin.

After fermentation, the mycelium is recovered by draining and filtration (or centrifugation), washed with water and then extracted three times by trituration with alcohol (ethanol or methanol). It is found that 90% by weight of the antibiotic is contained in the mycelium and 10% in the liquid of the culture medium. The antibiotic can be recovered from the liquid of the culture medium by extraction with normal butanol.

The antibiotic extract is freed from solvent at a temperature below 50° C. in the absence of light. The residue of the alcoholic extracts is first extracted with hexane (or petroleum ether) and then treated with chloroform in order to extract an unwanted antibacterial polypeptide substance. This polypeptide antibiotic was found, in the course of previous investigations, to be of no particular interest, for which reason it is discarded. The residue is then treated with diethylether and dried in air.

Purification can also be effected by molecular filtration chromatography on "Merkogel" 500 or "Sephadex" LH-20, using dimethylformamide as eluent. The eluates are detected either with a Pye Unicam universal wire detector or with an ultraviolet absorptiometer at 460 m$\mu$.

The fractions containing the antifungal substance are concentrated in vacuo ($10^{-1}$ mm.Hg.) at 40° C. and precipitated with diethyl ether. The precipitate is then centrifuged and washed three times with diethyl ether in order to eliminate all traces of dimethylformamide.

Lucknomycin can also be purified by countercurrent separation, using the solvent system comprising, by volume 35 parts pyridine, 65 parts ethyl acetate and 83 parts water in a Craig 100-tube countercurrent distribution machine, and subjecting it to 261 transfers. The optical densities of the bottom and top phases are measured; only one peak is observed. The fractions containing the antibiotic are combined and evaporated to dryness under reduced pressure. The resulting residue (golden yellow powder) is finally washed with a small amount of hot methanol.

Melting point: browns without melting starting from 150° C. (decomposition).

We claim:

1. Lucknomycin, an antifungal and antiprotozoal antibiotic, which:
    a. is an orange yellow powder;
    b. starts to decompose at about 150° C. but, even at 300° C., does not melt;
    c. has a molecular weight of about 1240;
    d. has the following elemental analysis: C, 58.92, H, 7.58; N, 2.29;
    e. is soluble in pyridine, dimethylformamide and dimethylacetamide, less soluble in 60% methanol, concentrated ethanol and isopropanol and is insoluble in benzene, acetone, water, chloroform, absolute ethanol, cyclohexane, ethyl acetate and diethyl ether;

f. gives an intense blue coloration in sulfuric acid;
g. has the following infrared absorption spectrum in a KBr pellet (in cm$^{-1}$):

| 3400 (S) | 1465 (W) | 1075 (S) |
|---|---|---|
| 3100 (W) | 1390 (W) | 1045 (W) |
| 2930 (S) | 1350 (W) | 1010 (S) |
| 2860 (M) | 1325 (W) | 995 (W) |
| 1715 (M) | 1295 (W) | 940 (W) |
| 1650 (M) | 1250 (W) | 890 (W) |
| 1600 (S) | 1185 (S) | 850 (M) |
| 1575 (W) | 1140 (W) | 835 (W) |
| 1545 (W) | 1110 (M) | 800 (W) | wherein S means strong absorption, M medium absorption and W weak absorption;

h. has the following ultraviolet absorption spectrum taken at a concentration of 1 mg. per 100 ml. of dimethylformamide;

344 mµ ($\epsilon = 3.5 \times 10^4$)

364 mµ ($\epsilon = 5.52 \times 10^4$)

384 mµ ($\epsilon = 8.04 \times 10^4$)

408 mµ ($\epsilon = 6.6 \times 10^4$)

i. has an optical rotation $[\alpha]_D^{25°C} = 187°$ to $194°$ (C = 0.3% in dimethylformamide at 25° C); and j. is an aromatic heptaene giving by retroaldolization reaction p-N-methylamino-acetophenone and which contains mycosamine as a substituent and which has no titratable carboxyl group.

2. An antifungal and antiprotozoal composition which comprises an effective amount of lucknomycin according to claim 1 in admixture with a pharmaceutically acceptable carrier.

3. The antifungal and antiprotozoal antibiotic lucknomycin, according to claim 1, in its essentially pure form.

4. A process for making the antifungal and antiprotozoal antibiotic defined in claim 1, which comprises cultivating *Streptomyces diastatochromogenes* var. Krains CBS 101.74, in an aqueous nutrient medium under submerged aerobic conditions until substantial antifungal and antiprotozoal antibiotic activity is imparted to said medium by the production of lucknomycin.

5. A process according to claim 4, which comprises cultivating *Streptomyces diastatochromogenes* var. Krains CBS 101.74, in an aqueous nutrient medium containing a source of assimilable carbon and a source of assimilable nitrogen under submerged aerobic conditions until substantial antifungal and antiprotozoal antibiotic activity is imparted to said medium by the production of lucknomycin and isolating the lucknomycin so produced.

6. A process according to claim 5, in which the isolation comprises filtering the medium to obtain a solid residue and a filtrate, extracting the solid residue with a lower alkanol, concentrating the extract, treating the residue successively with hexane, chloroform and diethyl ether to eliminate an antibacterial polypeptide substance and recovering lucknomycin from said residue.

7. A process according to claim 6, in which lucknomycin is recovered from the filtrate by extraction with normal butanol.

* * * * *